US00PP35394P2

(12) United States Plant Patent
Goffreda et al.

(10) Patent No.: US PP35,394 P2
(45) Date of Patent: Sep. 26, 2023

(54) PEACH TREE NAMED 'NJ362'

(50) Latin Name: ***Prunus persica* L.**
Varietal Denomination: NJ362

(71) Applicant: RUTGERS, THE STATE UNIVERSITY OF NEW JERSEY, New Brunswick, NJ (US)

(72) Inventors: Joseph C. Goffreda, Columbus, NJ (US); Anna M. Voordeckers, East Windsor, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 17/994,602

(22) Filed: Nov. 28, 2022

(51) Int. Cl.
*A01H 5/08* (2018.01)
*A01H 6/74* (2018.01)

(52) U.S. Cl.
USPC ..... Plt./196

(58) Field of Classification Search
USPC ..... Plt./194, 195, 196
See application file for complete search history.

*Primary Examiner* — Susan McCormick Ewoldt
(74) *Attorney, Agent, or Firm* — Patrick J. Daugerty; Daughety & Del Zoppo Co. LPA

(57) ABSTRACT

A new and distinct peach variety of *Prunus persica* named 'NJ362' is provided. This variety is distinguished from other peach varieties by its unique combination of non-showy flowers, medium to large, round, freestone fruit, with a greyed-red to greyed-purple blush over a yellow-white ground, ripening in late-season, and possessing sweet, sub-acid flavor.

6 Drawing Sheets

STATEMENT REGARDING FEDERALLY SPONSORED RESEARCH OR DEVELOPMENT

This invention was made with government support under, contract or grant Multistate Research Project NE-9, entitled Conservation and Utilization of Plant Genetic Resources, awarded or sponsored by the National Institute of Food and Agriculture. The government has certain rights in the invention.

Latin name of genus and species of the plant claimed: *Prunus persica* L.

Variety denomination: 'NJ362'.

BACKGROUND OF THE INVENTION

The present invention relates to a new and distinct variety of peach tree named 'NJ362' that resulted from crossing a peach seedling selection 'NJ354' (U.S. Plant Pat. No. 23,669) as the seed parent with 'H31-122-01232' (non-patented). The new variety differs from seed parent 'NJ354' (U.S. Plant Pat. No. 23,669) in that the new variety produces white fleshed fruit and has a sweeter flavor with rose-like aromatics. The new variety differs from pollen parent 'H31-122-01232' in that the new variety ripens about 4 weeks later and more consistently produces fruit. The resulting tree was selected when growing in a cultivated area as the fifty-second ($52^{nd}$) tree in the eighth ($8^{th}$) row of Block H at a fruit research farm in Cream Ridge, N.J.

BRIEF SUMMARY OF THE INVENTION

'NJ362' differs from the related cultivar 'White Lady' (U.S. Plant Pat. No. 5,821), in that trees of 'NJ362' crop more consistently and are less susceptible bacterial leaf spot (*Xanthomonas campestris* pv. *pruni*) than 'White Lady'. The 'NJ362' variety is also distinguished from other peach varieties due to the following unique combination of characteristics:

Produces medium to large, nearly round, freestone fruit with a low tendency to split when adequately cropped.

Fruits have an attractive greyed-red to greyed-purple blush over a bright yellow-white ground color.

Excellent production of fruit that ripen in late-season on trees with low susceptibility to bacterial leaf spot.

Fruit have superior eating quality due to their aromatic, sweet, and sub-acid flavor.

The variety was asexually reproduced at a fruit research farm in Cream Ridge, N.J. Asexual reproduction of this new variety by budding onto 'Lovell' peach seedling rootstock (non-patented) shows that the foregoing characteristics are so reproduced.

The following detailed description concerns the original tree, 'NJ362'. The original tree has been observed growing in a cultivated area at a fruit research farm in Cream Ridge, N.J. Its asexual progeny have been observed growing in a cultivated area in Cream Ridge, N.J and Aspers, Pa. Certain characteristics of this variety, such as growth and color, may change with changing environmental conditions (such as, light, temperature, moisture, nutrient availability) or other factors. Color descriptions and other terminology are used in accordance with their ordinary dictionary descriptions unless the context clearly indicates otherwise. Color designations are made with reference to The Royal Horticultural Society (RHS) Colour Chart (1966 Ed.)

BRIEF DESCRIPTION OF THE DRAWINGS

This new variety is illustrated by the accompanying photographic drawings of the 'NJ362' plant in its sixth leaf, depicting the peach tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
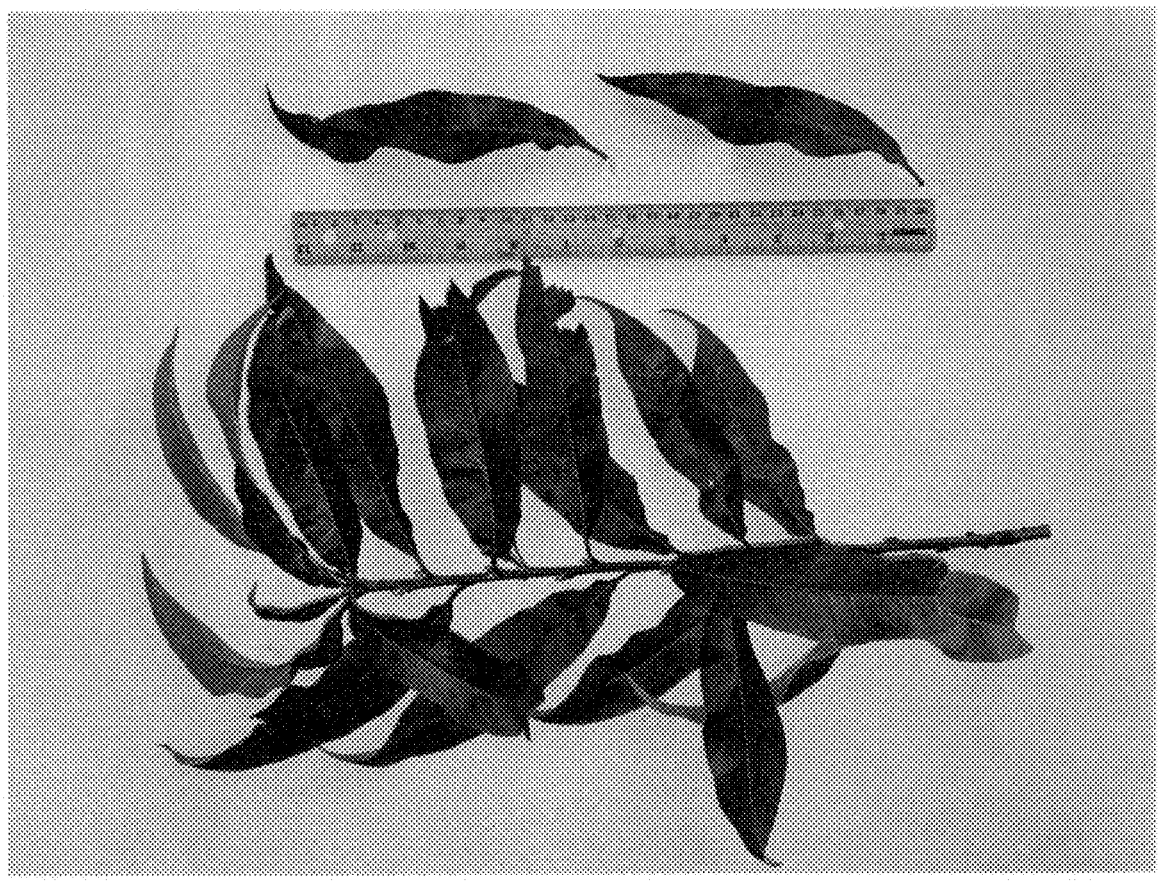
FIG. 1 is a color photograph taken on Oct. 14, 2022, of a characteristic twig of 'NJ362' bearing typical leaves of the foliage.
Figure 2:
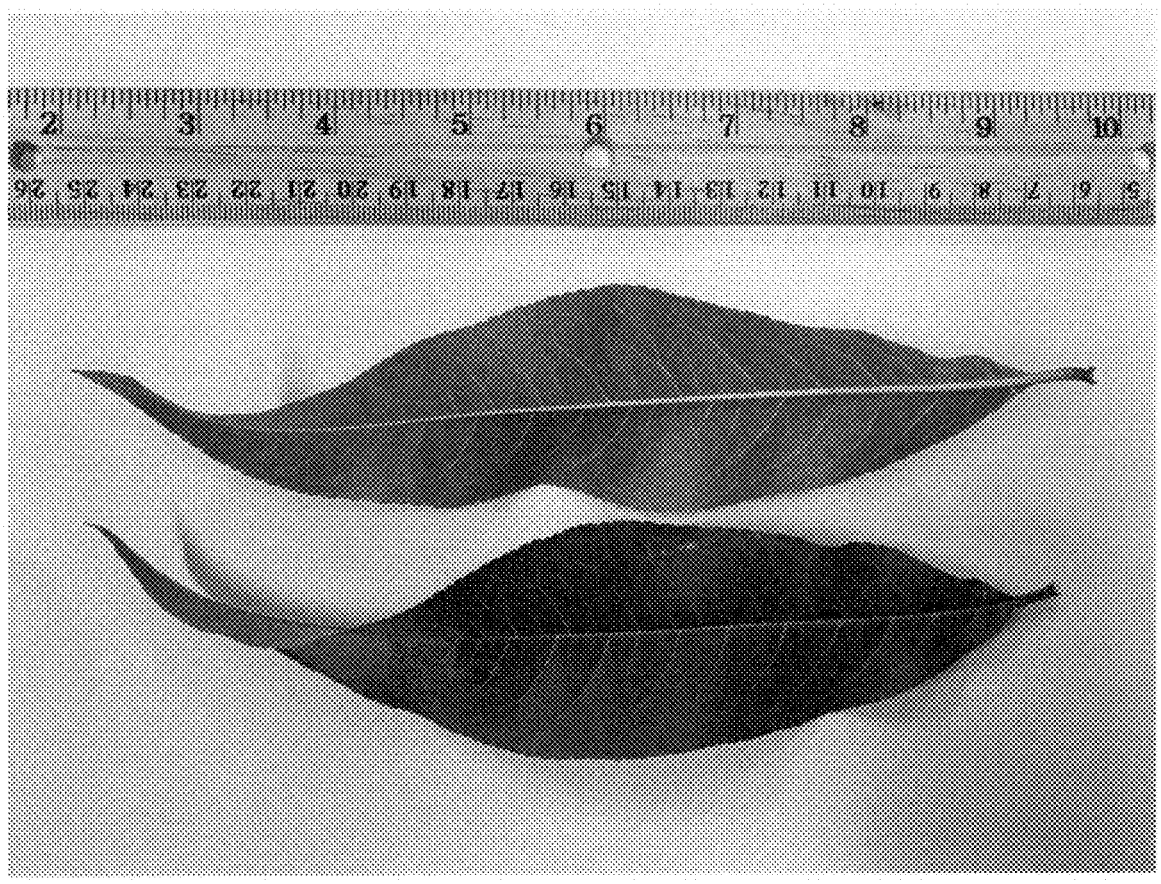
FIG. 2 is a color photograph taken on Oct. 14, 2022, of characteristic leaves of 'NJ362'. The leaves are presented in two positions, showing both the upper leaf surface and underside of the leaf.
Figure 3:
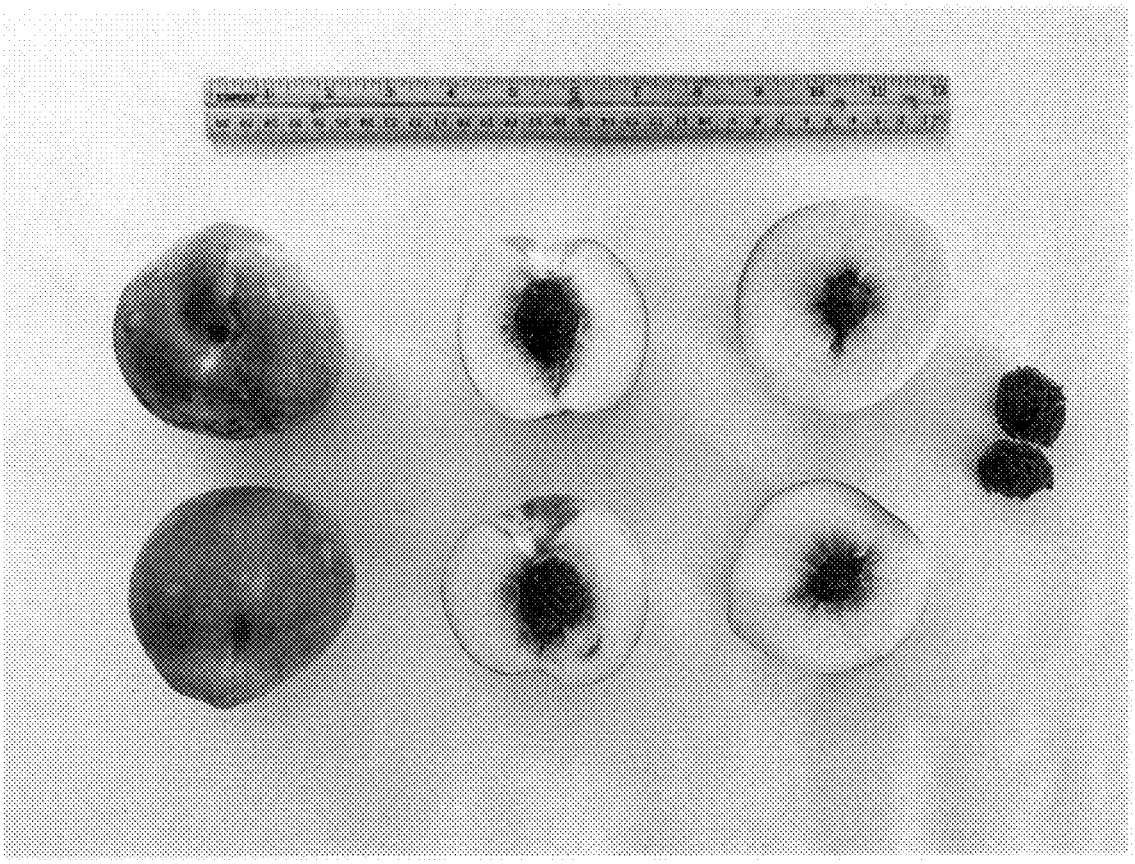
FIG. 3 is a color photograph taken on Sep. 16, 2022, of characteristic mature fruit and stones of 'NJ362'. Whole fruit are presented in two positions and both a transverse and longitudinal cross section. The stones exemplify the obovate shape and pits and grooves on the surface of the stone.
Figure 4:
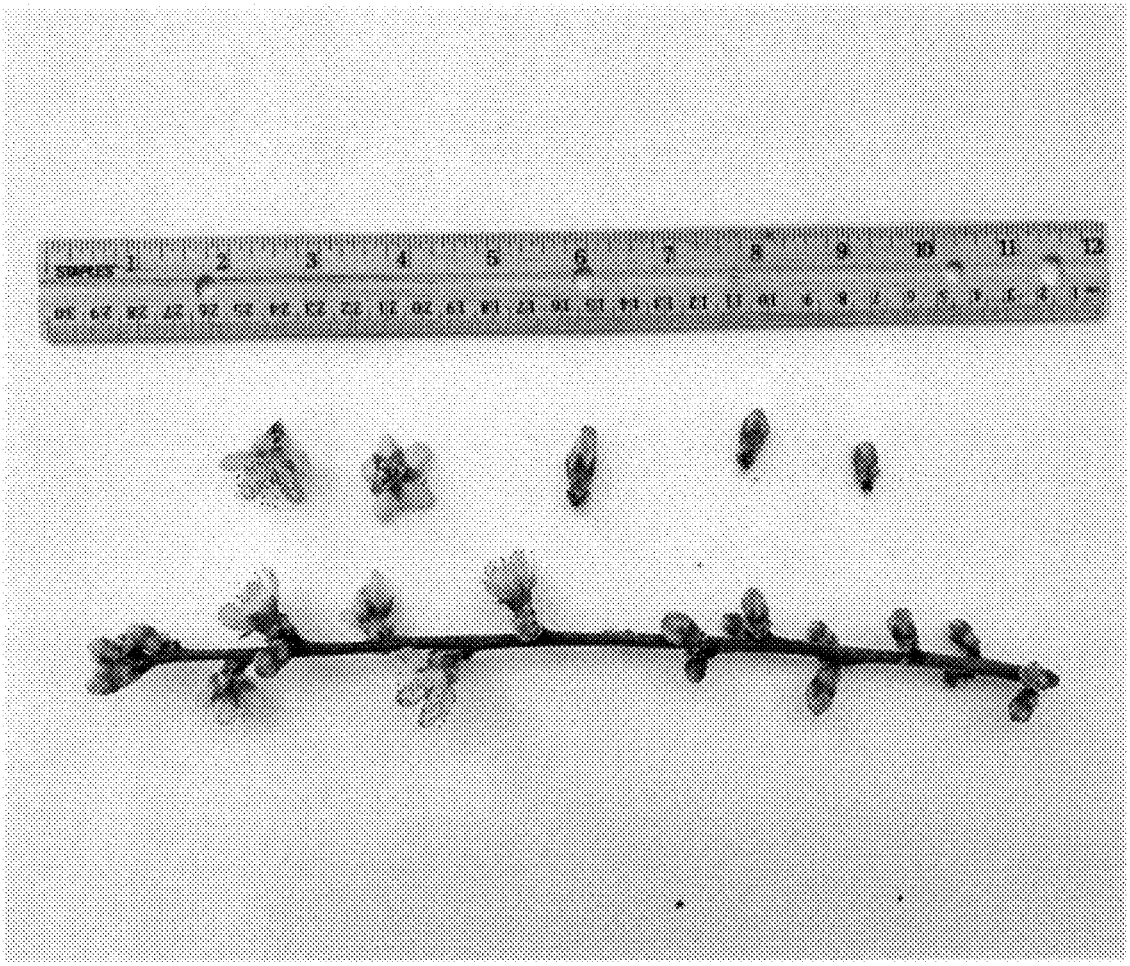
FIG. 4 is a color photograph of a characteristic twig that illustrates the typical flower buds and small, non-showy flowers of 'NJ362' observed on a tree in the test block at Adams County Nursery in Aspers, Pa. on Apr. 12, 2022.
Figure 5:
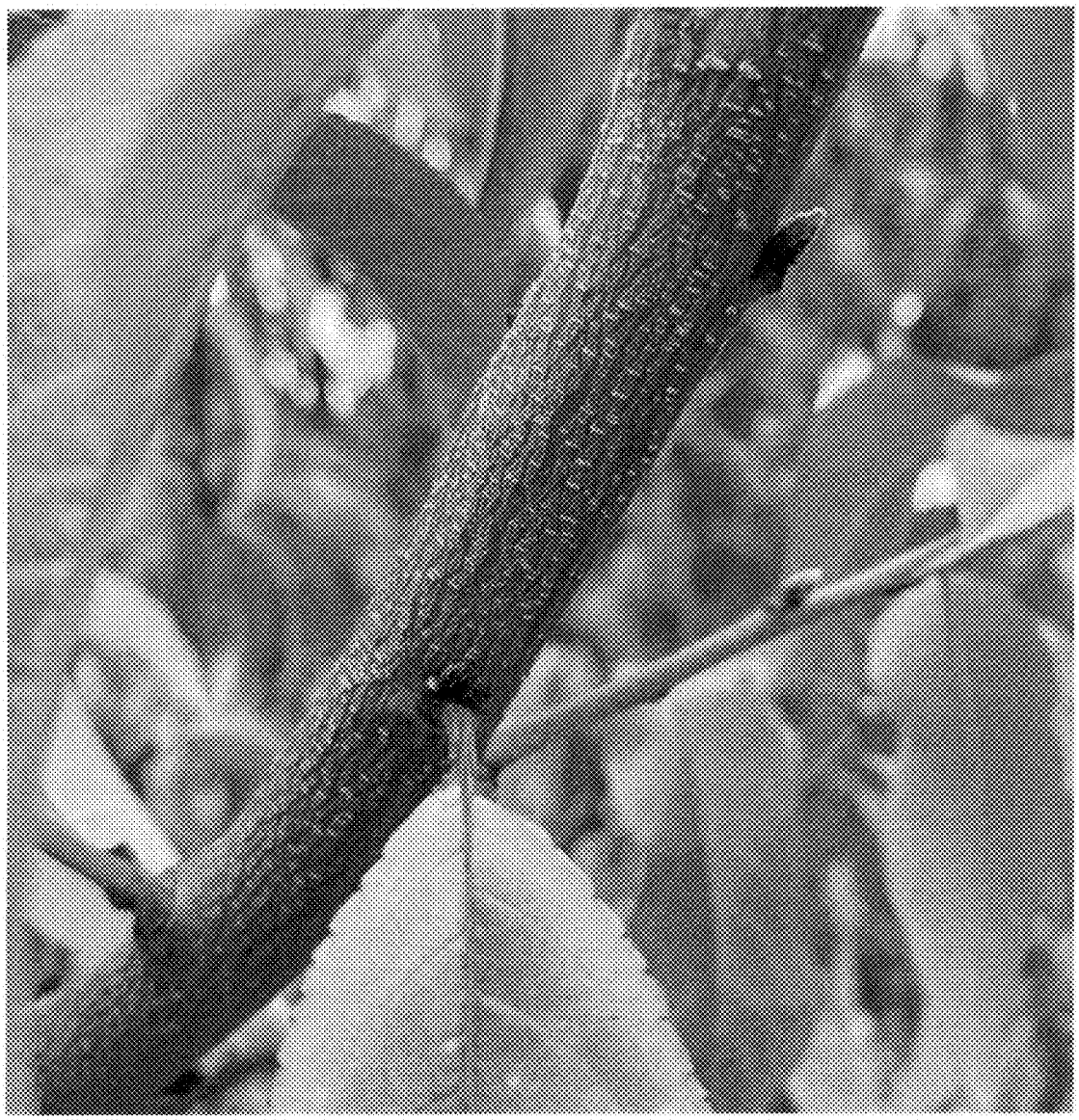
FIG. 5 is a color photograph taken on Oct. 17, 2022, of immature bark of 'NJ362' that illustrates color and the moderate density of elliptic lenticels on the immature bark.
Figure 6:
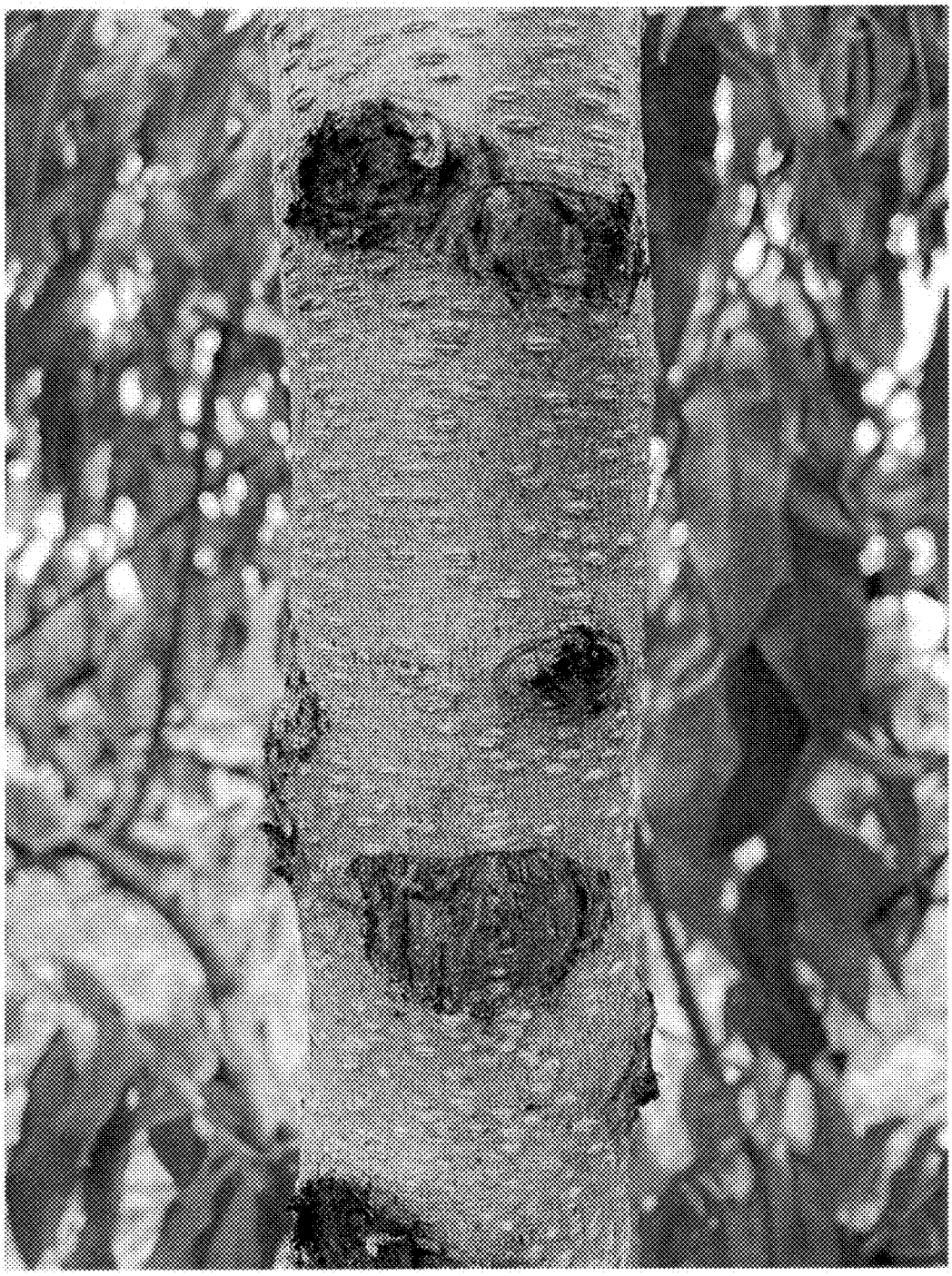
FIG. 6 is a color photograph taken on Oct. 17, 2022, of mature bark of 'NJ362' that illustrates the greyed-green color and rough texture of the mature bark.

The colors of and illustration of this type may vary with lighting and other conditions and, therefore, color characteristics of this new variety should be determined with reference to the observations described herein, rather than from these illustrations alone.

DETAILED BOTANICAL DESCRIPTION

The following detailed description of the 'NJ362' variety is based on observations of an asexually reproduced tree. The observed tree was in its sixth leaf and growing on 'Lovell' rootstock (non-patented) in a test block at Adams County Nursery, Inc. in Aspers, Pa.

Scientific name: *Prunus persica* L.

Parentage: Seed parent 'NJ354'; Pollen parent 'H31-122-01232'.

Tree:

*Plant hardiness zone.*—Growth of plants has only been observed in zone 6b.

*Chilling requirement.*—Aspers, Pa., receives about 2300 chilling hours (hours between 32- and 45-degrees Fahrenheit) between November 1 and March 31 each year. This is based on hourly temperature data collected from 2006 to 2020 by the National Oceanic and Atmospheric Administration. Due to the physiology of 'NJ362', the chilling requirements of the plant could be lower than the annually acquired 2300 hours. The minimum chilling requirement of the cultivar is unable to be determined because it is limited by the chilling hours accumulated at the growing location in Aspers, Pa.

*Drought and heat tolerance.*—'NJ362' tolerates heat and drought conditions found on unirrigated ground in Aspers, Pa., which generally experiences drought conditions for 2-3 weeks each summer and occasional daytime high temperatures in the upper 90 degrees Fahrenheit.

*Overall shape.*—Spreading.

*Height.*—Average as compared to other peach cultivars.

*Width.*—Average as compared to other peach cultivars.

Trunk and branches:

*Trunk diameter.*—10.2 cm. at 16 cm above the soil line.

*Trunk bark color.*—Horizontal striping pattern with combination of colors from greyed-green RHS groups 196, 197, and 198.

*Primary branches.*—Greyed-green (RHS 197C) heavily mottled over greyed-orange (RHS 176A).

*Lenticels.*—Moderate density, elliptic shape, Greyed-green (RHS 196C) on thin outer edge and Greyed-orange (between RHS 173B and RHS 173C) in center.

*Branch pubescence.*—None.

*New growth bark.*—Greyed purple (between RHS 183A and RHS 183B).

Leaves:

*Arrangement.*—Alternately on the branch.

*Texture.*—Glabrous, both surfaces.

*Sheen.*—Young leaves satin to semi-glossy with a flat finish on the underside.

*Length.*—About 177 mm. to 198 mm., averaging about 189 mm., including the petiole.

*Width.*—About 41 mm. to 49 mm., averaging about 46 mm.

*Petiole.*—About 7 mm to 14 mm, averaging about 11 mm. Color: Yellow-green (between RHS 145B and RHS 145C).

*Margin.*—Crenate.

*Margin undulation.*—Low.

*Form.*—Lanceolate, and concave in cross section.

*Apex.*—Sharply acute, curved downward.

*Base.*—Acute.

*Venation.*—Pinnate.

Glands:

*Number.*—About 2 to 4, averaging about 3.2.

*Position.*—Mostly located on the petiole, with some located at the leaf base.

*Size.*—Length averaging about 1 mm. in length.

*Form.*—Reniform.

Leaf color:

*Upper leaf surface.*—Green (RHS 137A).

*Lower leaf surface.*—Green (RHS 138A).

*Vein.*—Yellow-green (RHS 145C).

*Pubescence.*—None.

Flowers:

*Size.*—Typical flower measures between 17 mm. and 20 mm., averaging about 22 mm. across the flower opening.

Color:

*Pink stage bud.*—Red-purple (between RHS 57C and RHS 57D).

*Open flower.*—Red-purple (RHS 65B); Upper and lower petal surfaces light reddish purple (RHS 74D).

*Petals.*—Typically five petals per flower; slightly cupped, narrow elliptic, averaging about 11 mm. long and 7 mm. wide.

*Petal base.*—Acuminate.

*Petal apex.*—Rounded.

*Petal margin.*—Entire, with slight undulation on some petals.

*Petal texture.*—Smooth.

Stamens:

*Number.*—Variable, typical range 46 to 55, averaging about 50.

*Position.*—Perigynous and near the point of attachment of the petals.

*Length.*—Between 11 mm. and 12 mm., averaging 11.4 mm.

*Filament color.*—Red-purple (RHS 68D).

Pistil:

*Number.*—One.

*Size.*—Length between 15 mm. and 19 mm., averaging 17 mm.

*Style color.*—Yellow (RHS 12D).

*Stigma color.*—Yellow-orange (RHS 16C).

*Ovary.*—About 2 mm. in length and ellipsoid in shape, color yellow-green (between RHS 154C and RHS 154D).

*Ovary pubescence.*—Length short, fine, with moderate density at base of style and apex of ovary.

Sepals:

*Number.*—Five.

*Sepal pubescence.*—Length short, fine, with moderate density.

*Color.*—Red-purple (RHS 59B).

*Shape.*—Triangular, with a rounded apex.

*Size.*—Length averaging 6 mm., width averaging 4 mm. at base.

*Nectar cup color.*—Yellow-orange (RHS 22A).

*Fragrance.*—Nearly none.

*Bloom season.*—Full bloom on Apr. 12, 2022, in Aspers, Pa. Flower buds were swollen on Mar. 1, 2023, and full bloom began on Apr. 1, 2023, in Aspers, Pa.

Fruit:

*Size.*—Medium to large, averaging about 6.9 centimeters (cm.) long (parallel to the suture) and 7.8 cm. wide (perpendicular to the suture).

*Longitudinal section.*—Nearly round.

*Traverse section.*—Nearly round.

*Suture.*—Shallow.

*Apex.*—Indented.

Skin:

*Thickness.*—Medium.

*Surface.*—Pubescent, moderate density, typically less than 1 mm. in length.

*Astringency.*—None.

*Tendency to crack.*—Low.

*Color.*—Blush is Greyed-red (between RHS 181B and RHS 181C) in partial sun; greyed-purple (between RHS 187A and RHS 187B) in full sun; ground color is yellow-white (RHS 158A).

*Fruit properties.*—

*Flesh color.*—Yellow-white (between RHS 158C and RHS 158D), mottled with red (RHS 53B) in the flesh and adjacent to stone.

*Flesh adhesion.*—Freestone.

*Juice.*—Moderate.

*Texture.*—Firm but melting.

*Fibers.*—Not noticeable.

*Ripens.*—Between September 13 and September 20 in Aspers, Pa.

*Flavor.*—Sweet, subacid.

*Aroma.*—Moderate.

*Eating quality.*—Very good.

*Usage.*—Dessert.

*Market.*—Local and long distance.

*Productivity.*—Excellent, though varies greatly depending upon conditions inclusive of winter and spring temperatures, rainfall, tree density, pruning methods, soil type, fertilization, irrigation, and degree of fruit thinning.

Stone:

*Type.*—Freestone.

*Form.*—Obovate.

*Surface.*—Pits and grooves.

*External color.*—Greyed-orange (between RHS 177A and RHS 177B). Some grooves are Greyed-red (RHS 178A).

*Cavity surface color.*—Greyed-orange (between RHS 165C and RHS 165D).

*Size.*—Averages about 33.7 mm. long and 25.2 mm. wide.

*Tendency to split.*—Typically low.

Kernel:

*Form.*—Obovate.

*Skin color.*—Greyed-orange (RHS 165C).

*Vein color.*—Greyed-orange (between RHS 165A and RHS 165B).

*Size.*—Averages about 17.1 mm. long, 10.7 mm. wide, and 4.6 mm. in breadth.

*Plant/fruit disease and pest resistance/susceptibility.*—No atypical resistances/susceptibilities have been noted under normal cultural practices.

We claim:

1. A new and distinct variety of peach tree named 'NJ362', substantially as herein shown and described.

* * * * *